US012685805B2

(12) United States Patent
Conway et al.

(10) Patent No.: US 12,685,805 B2
(45) Date of Patent: Jul. 21, 2026

(54) SYSTEM FOR CONTROL OF A BLOOD GAS EXCHANGER

(71) Applicants: UNIVERSITY OF MARYLAND, BALTIMORE, Baltimore, MD (US); University of Maryland Medical Center, LLC, Linthicum, MD (US)

(72) Inventors: R. Gregory Conway, Baltimore, MD (US); Bartley Griffith, Gibson Island, MD (US); Zhongjun Wu, Marriottsville, MD (US)

(73) Assignees: University of Maryland, Baltimore, Baltimore, MD (US); University of Maryland Medical Center, LLC, Linthicum, MD (US)

( * ) Notice: Subject to any disclaimer, the term of this patent is extended or adjusted under 35 U.S.C. 154(b) by 917 days.

(21) Appl. No.: 17/253,673

(22) PCT Filed: Jun. 20, 2019

(86) PCT No.: PCT/US2019/038095
    § 371 (c)(1),
    (2) Date: Dec. 18, 2020

(87) PCT Pub. No.: WO2019/246320
    PCT Pub. Date: Dec. 26, 2019

(65) Prior Publication Data
    US 2021/0260266 A1      Aug. 26, 2021

Related U.S. Application Data

(60) Provisional application No. 62/687,484, filed on Jun. 20, 2018.

(51) Int. Cl.
    *A61M 1/16*        (2006.01)
    *A61M 1/36*        (2006.01)

(52) U.S. Cl.
    CPC ......... *A61M 1/1698* (2013.01); *A61M 1/3666* (2013.01); *A61M 2205/3334* (2013.01); *A61M 2230/202* (2013.01); *A61M 2230/205* (2013.01)

(58) Field of Classification Search
    CPC  A61M 1/1698; A61M 1/3666; A61M 60/113; A61M 60/38; A61M 1/1678;
    (Continued)

(56) References Cited

U.S. PATENT DOCUMENTS 5,632,281 A * 5/1997 Rayburn ............. A61B 5/0836
                                                   600/543
5,810,759 A * 9/1998 Merz .................. A61M 1/1698
                        (Continued)

OTHER PUBLICATIONS

International Search Report issued in corresponding International Application No. PCT/US2019/038095 on Oct. 3, 2019.

*Primary Examiner* — Michael J Tsai
*Assistant Examiner* — Kathleen Paige Farrell
(74) *Attorney, Agent, or Firm* — Whiteford, Taylor & Preston, LLP; Peter J. Davis

(57) ABSTRACT

A demand-adapting and auto-regulatory ECMO system and method is disclosed that may be configured to provide complete cardiopulmonary replacement. The system and method employ a blood gas exchanger having a blood inlet, a blood outlet, a gas inlet, and a gas outlet, an oxygen sensor positioned to detect oxyhemoglobin saturation at the blood inlet, and a carbon dioxide sensor positioned to detect exhaust gas CO2 concentration at the gas outlet. A controller communicates with the oxygen sensor and the carbon dioxide sensor and controls blood flow and gas flow through the blood gas exchanger in response to a sensed oxygen level by the oxygen sensor and a sensed carbon dioxide level by the carbon dioxide sensor, in turn maintaining the sensed oxy-
(Continued)

gen level and the sensed carbon dioxide level within a pre-designated range of values to maintain a patient's metabolic requirements.

19 Claims, 7 Drawing Sheets

(58) Field of Classification Search
CPC .............. A61M 1/28; A61M 2230/202; A61M 2230/205; A61M 2205/3334; A61M 1/3656; A61M 2202/0208; A61M 2202/0225; A61M 1/3623; A61M 2205/502; A61M 1/3609; A61B 5/14542; A61B 5/0836; A61B 5/14551; A61B 5/1495
See application file for complete search history.

(56) References Cited

U.S. PATENT DOCUMENTS

| | | | |
|---|---|---|---|
| 2004/0030277 A1* | 2/2004 | O'Mahony ............. | A61M 1/34 |
| | | | 210/741 |
| 2005/0103342 A1* | 5/2005 | Jorczak ............. | A61M 16/0672 |
| | | | 128/205.24 |
| 2012/0090611 A1* | 4/2012 | Graboi et al. ........ | A61M 16/12 |
| 2015/0034082 A1* | 2/2015 | Kimm ............... | A61M 16/0051 |
| | | | 128/202.16 |
| 2016/0242680 A1* | 8/2016 | Arif et al. .............. | A61B 5/746 |
| 2017/0049618 A1* | 2/2017 | Ward et al. ........ | A61B 5/14542 |
| 2017/0252505 A1* | 9/2017 | Wu ..................... | A61M 1/1698 |

\* cited by examiner

SYSTEM FOR CONTROL OF A BLOOD GAS EXCHANGER

CROSS REFERENCE TO RELATED APPLICATION

This application claims the benefit of U.S. Provisional Application No. 62/687,484 titled "System for Control of a Blood Gas Exchanger," filed Jun. 20, 2018 by the inventors herein, which application is incorporated herein by reference in its entirety.

STATEMENT ON GOVERNMENT SUPPORT

This invention was made with government support under grant numbers HL007698 and HL118372 awarded by the National Institutes of Health. The government has certain rights in the invention.

FIELD OF THE INVENTION

The current invention relates to demand-adapting control of blood gas exchangers, and more particularly to a method and system for automatically controlling the exchange of gasses in a paracorporeal blood gas exchanger, such as an artificial lung system.

BACKGROUND

Extracorporeal Membrane Oxygenation (ECMO) is successful in providing the cardiopulmonary support necessary to bridge critically ill patients to definitive therapy. As shown in FIG. 1, such ECMO entails positioning a blood flow circuit (shown generally at 10), including a pump 12 and a blood gas exchanger 14, in parallel with the patient's native circulation. In typical ECMO configurations, a portion (shown by arrow 16) of the patient's blood flow is shunted past the ECMO circuit, and this shunted portion of blood flow can significantly reduce gas exchange. As a result of the fine control that is thus necessary to maintain proper gas exchange, ECMO is typically administered in the intensive care unit, in support of both patients with respiratory failure and cardiopulmonary failure, and long-term administration of ECMO in this setting is commonly performed by highly-trained personnel.

Efforts are underway to develop ECMO systems that will adequately support patients outside of the ICU, and eventually outside of the hospital. Administration of ECMO therapy in these settings is challenged by two factors: first, patients with increased mobility may exhibit greater fluctuation in gas-exchange requirements; and second, the expertise required to adjust the ECMO settings may not be readily available. As such, a successful out-of-ICU ECMO system will require a mechanism to detect the required level of ECMO support, as well as a means to automatically adapt the settings of the ECMO system to the patient's requirements. Current systems of adapting ECMO support to patient needs typically use an expensive and large online blood-gas monitoring system, which typically require additional, invasive blood-contacting sensors that increase the risk of complications for the patient, cost, and potential failure points. Thus, there remains a need in the art for an adapting ECMO support system that eliminates the need for this additional invasive and blood-contacting equipment.

SUMMARY OF THE INVENTION

Provided is a system and method configured to solve one or more of the problems associated with long-term administration of ECMO outside the hospital. Thus, a demand-adapting and auto-regulatory ECMO system in accordance with certain aspects of an exemplary embodiment of the invention is described herein in use with an ovine model with neutralized native lung function. The system may be configured to provide complete cardiopulmonary replacement. The demand-adapting and auto-regulatory ECMO system has the potential to provide a survival advantage in ambulatory animals and ambulatory patients, when compared to a standard non-adaptive ECMO system.

Currently, typical ECMO flow circuits sit in parallel with the native circulation, and there is a fraction of blood that bypasses the ECMO circuit. With alterations in cardiac output, the proportion of blood that bypasses the ECMO circuit varies, and has the potential to significantly reduce the amount of oxygen delivered to systemic tissues. Systems and methods according to certain embodiments of the invention include employing a demand-adapting and auto-regulatory ECMO system and method that relies on minimizing the blood that bypasses the ECMO circuit, thus consistently providing gas exchange to a high proportion of circulating blood. When applied to a portable ECMO system, for example, the demand-adapting and auto-regulatory system and method increases patient mobility and safety compared to typical ECMO systems.

Thus, systems and methods according to various embodiments can be used for, by way of non-limiting example, one or more of the following: automation of cardiopulmonary bypass; automation of Extracorporeal Membrane Oxygenation (ECMO); enhancing the performance of a respiratory assist device for patients with lung failure; enhancing the performance of a circulatory assist device for patients with cardiopulmonary failure; increasing the portability of respiratory or circulatory assist devices; and providing a means for non-skilled personnel to administer ECMO therapy.

In accordance with further aspects of an embodiment, an auto-regulatory system for the control of a blood gas exchanger is provided comprising: a blood gas exchanger having a blood inlet, a blood outlet, a gas inlet, and a gas outlet; an oxygen sensor positioned to detect oxyhemoglobin saturation at the blood inlet; a carbon dioxide sensor positioned to detect exhaust gas $CO_2$ concentration at the gas outlet; a fluid pump in fluid communication with the blood gas exchanger; a gas delivery system in fluid communication with the blood gas exchanger; and a controller in communication with the oxygen sensor, the carbon dioxide sensor, the fluid pump and the gas delivery system and configured to control the pump and the gas delivery system in response to a sensed oxygen level by the oxygen sensor and a sensed carbon dioxide level by the carbon dioxide sensor to maintain the sensed oxygen level and the sensed carbon dioxide level within a pre-designated range of values to maintain a patient's metabolic requirements.

In accordance with still further aspects of an embodiment, an auto-regulatory system for the control of a blood gas exchanger is provided, comprising: a blood gas exchanger having a blood inlet, a blood outlet, a gas inlet, and a gas outlet; an oxygen sensor positioned to detect oxyhemoglobin saturation at the blood inlet; a carbon dioxide sensor positioned to detect exhaust gas $CO_2$ concentration at the gas outlet; and a controller in communication with the oxygen sensor and the carbon dioxide sensor and configured to control blood flow and gas flow through the blood gas exchanger in response to a sensed oxygen level by the oxygen sensor and a sensed carbon dioxide level by the carbon dioxide sensor to maintain the sensed oxygen level and the sensed carbon dioxide level within a pre-designated range of values to maintain a patient's metabolic requirements.

In accordance with yet further aspects of an embodiment, a method is provided for auto-regulation of a blood gas exchanger, comprising the steps of: providing a blood gas exchanger having a blood inlet, a blood outlet, a gas inlet, and a gas outlet; an oxygen sensor positioned to detect oxyhemoglobin saturation at the blood inlet; a carbon dioxide sensor positioned to detect exhaust gas CO2 concentration at the gas outlet; and a controller in communication with the oxygen sensor and the carbon dioxide sensor and configured to control blood flow and gas flow through the blood gas exchanger in response to a sensed oxygen level by the oxygen sensor and a sensed carbon dioxide level by the carbon dioxide sensor to maintain the sensed oxygen level and the sensed carbon dioxide level within a pre-designated range of values to maintain a patient's metabolic requirements; receiving at the controller a blood flow rate of blood flowing to the blood gas exchanger and a sweep gas flow rate of sweep gas flowing to the blood gas exchanger; receiving at the controller a blood oxygen concentration from the oxygen sensor; receiving at the controller an exhaust gas CO2 concentration from the carbon dioxide sensor; and causing said controller to modify at least one of the blood flow rate and the sweep gas flow rate in response to and based upon the blood oxygen concentration and the exhaust gas CO2 concentration.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

DETAILED DESCRIPTION OF THE PREFERRED EMBODIMENTS

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
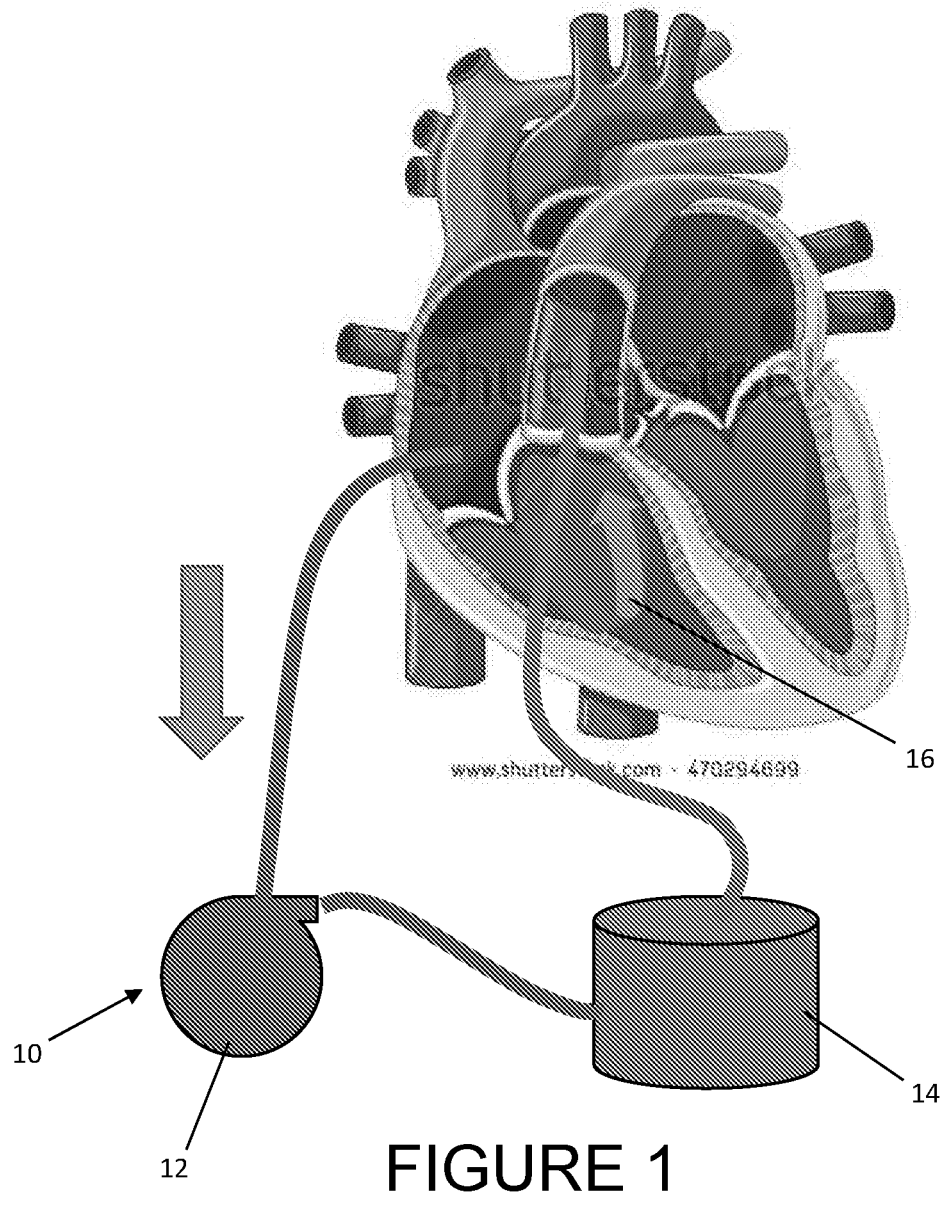
FIG. 1 is a schematic view of a typical ECMO circuit according to the prior art.
Figure 2:
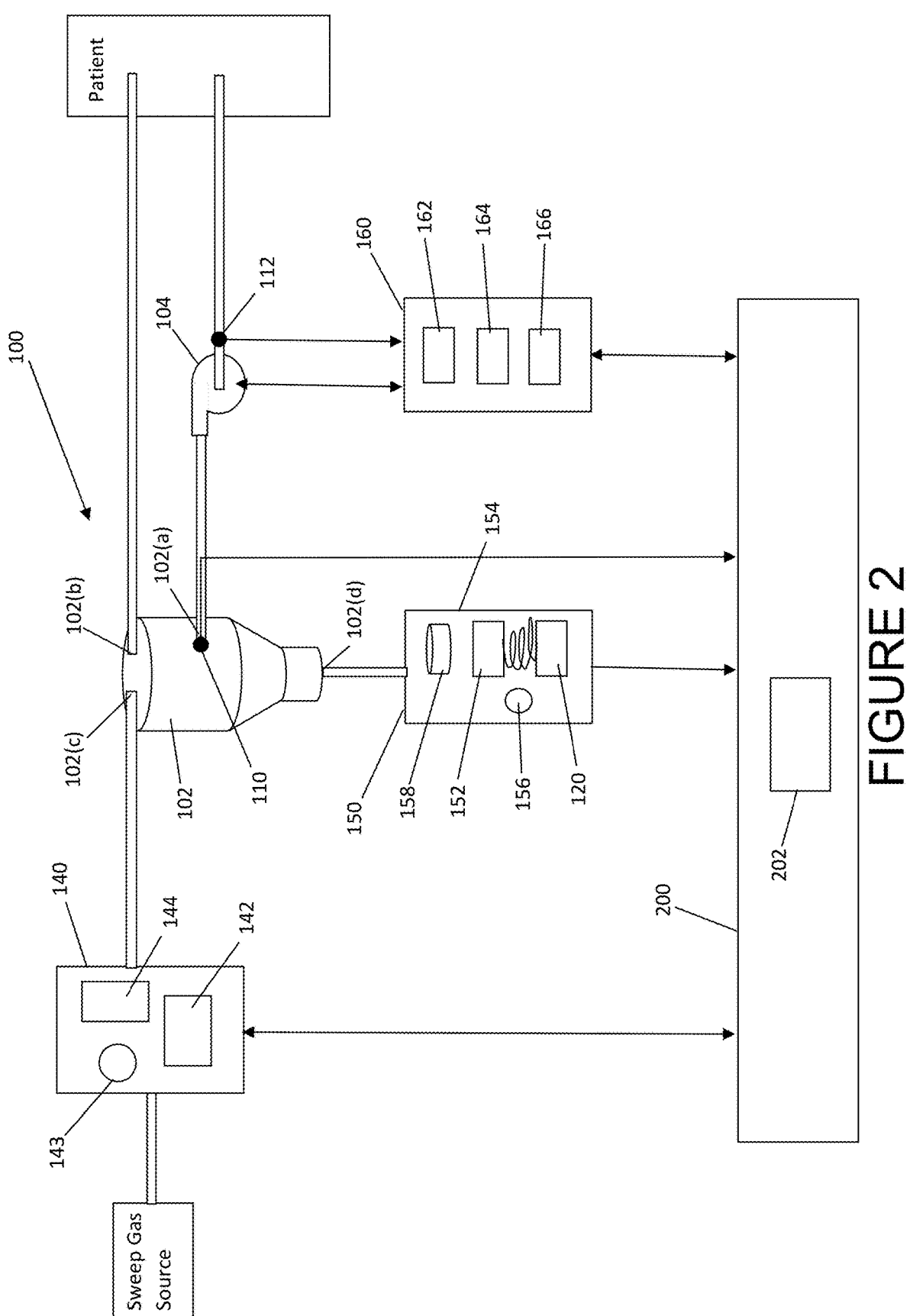
FIG. 2 is a schematic view of an auto-regulatory system for the control of a blood gas exchanger according to certain aspects of an embodiment of the invention.

With reference to FIG. 2, provided herein is a method and system for automatically controlling the blood flow and gas flow through a gas exchanger (e.g., a membrane oxygenator) to maintain targeted physiologic parameters within a patient. The system (shown generally at 100) is configured to operate using a minimal number of non-invasive sensors, such as an inlet oxyhemoglobin saturation (SvO2) sensor (i.e., blood oxygen sensor 110) and blood gas exchanger exhaust gas CO2 concentration sensor 120. In some embodiments, other sensors may be included, such as gas flowmeters, etc., as described in more detail below. Furthermore, maintaining some parameters, such as a partial pressure of exhaust gas (pCO2), may be based on adjustment of a blood:gas ratio, rather than an absolute gas flow rate as is typical.

The method and system can be used in many procedures and external flow devices, such as cardiopulmonary bypass, extracorporeal membrane oxygenation (ECMO), respiratory assist devices for patients with lung failure, circulatory assist devices for patients with cardiopulmonary failure, and the like. In certain configurations, the system includes a controller 200 and instructions (e.g., software) for performing embodiments of the method. In certain configurations, the controller may be a programmable microcontroller or embedded system, such as an Arduino Due or the like. The system 100 may also include varied additional components, such as a gas flow regulator 140, a blood flow regulator 160, sensory equipment, etc. Furthermore, other embodiments of the method may be implemented on an external controller or system computer, such as another ECMO or respiratory device. Still further, the method can be implemented on more than one controller or system computer, such as a personal computer.

The method is configured to automatically control the blood flow and gas flow through a gas exchanger 102 to maintain targeted physiologic parameters in response to sensor inputs. Gas exchanger 102 includes a blood inlet 102(*a*), a blood outlet 102(*b*), a gas inlet 102(*c*), and a gas outlet 102(*d*). In accordance with certain aspects of an embodiment, a method includes receiving blood and gas flow data, receiving $CO_2$ data, determining a blood flow target, and determining a gas flow target. In some embodiments, the method further includes calibrating the sensors in response to the blood and gas flow, $CO_2$ data, and targeted physiologic parameters. For example, the sensors can be calibrated to have offset or scaling parameters. The method further includes sending instructions to adjust the blood flow and the gas flow to substantially achieve the blood flow target and gas flow target, if necessary, and still further sending instructions to maintain the blood flow and gas flow to substantially maintain the blood flow and gas flow at the blood flow target and gas flow target, respectively.

According to certain aspects of an embodiment, receiving the blood flow data and gas flow data includes receiving a blood flow rate and a sweep gas, e.g., oxygen, flow rate from flow rate sensors. The blood flow rate and an oxygen flow rate are used within the control loops or systems (e.g., proportional-integral-derivative) to maintain the blood flow and gas flow at the target rates (or within ranges) or set-points. The set-points for the flows are determined either through a an automatic controller, such as a fuzzy controller (such as described below), or if the system is operating in a manual mode, through a manual setting.

Furthermore, receiving the blood flow data and gas flow data can include receiving targeted physiologic parameters from an external source, while in other embodiments reading stored targeted physiologic parameters.

Determining the blood flow target and the gas flow target according to certain aspects of an embodiment may include using a fuzzy logic control algorithm (FLCA). For example, the FLCA reads oxygenator inlet oxyhemoglobin saturation (SvO2) at blood oxygen sensor 110, oxygenator exhaust gas $CO_2$ concentration at $CO_2$ sensor 120, the blood flow rate at blood flow sensor 112, and the sweep gas flow rate at gas flow meter 142. The system 100 determines errors from these values to the set-point values, a first derivative of these errors with respect to time, and a variance in the blood flow. The system 100 converts these inputs (known as crisp inputs, since they are representative of real-world values) into fuzzy inputs through a process known as fuzzification. The fuzzification process determines the degree to which each fuzzified input belongs to a membership function, which translates the input value to a corresponding output value. Summation (such as using the centroid method, although other combination techniques are possible, as known in the art) of these outputs and defuzzification results in a crisp output. The crisp output is applied as a change to the set-point. For example, determining the blood flow rate can include: (1) reading the SvO2 from the blood oxygen sensor 110; (2) determining an error (E) or difference from the read SvO2 and the set-point, and determining the first derivative of the error (dE/dt); (3) determining the degree to which E and dE/dt belong to a membership function through fuzzification (e.g., an error of E=−5 may be considered as 70% "BIG NEGATIVE" and 30% "MEDIUM NEGA-TIVE"); (4) determining the output functions (represented as trapezoids or triangles), such as by evaluating all membership functions (e.g., an input of 70% "BIG NEGATIVE" may result in 60% "LARGE INCREASE", and an input of 30% "MEDIUM NEGATIVE" may result in an output of 40% "MODERATE INCREASE"); (5) determining the total change to blood flow, such as by combining the output functions using a centroid; (6) determining a new set-point by adding the total change of blood flow to the current set-point, and; (7) sending an instruction to the blood pump 104 to change the blood flow. Still further, determining the blood flow target and the gas flow target includes applying at least one rule based on defuzzifying the combined respective values to determine outputs or commands to adjust the blood flow and/or gas flow. As described above, the method includes sending instructions, which can include sending the outputs or commands to the pump 104, etc.

With regard to further aspects of an embodiment, the controller 200 is further configured to determine an estimated arterial partial pressure of carbon dioxide (pCO2) value when determining blood flow target and/or the gas flow target.

In one embodiment, the system is configured to externally control and/or monitor an external flow device. For example, controller 200 may be implemented on a client system (e.g., personal computer with Windows® operating system) as a software program to automatically or manually control the system and method according to embodiments of the invention. System 100 may interface the embedded controller 200 and external sensors (e.g., Medtronic® inline oxyhemoglobin saturation meter). The system 100 is further configured to receive input and custom parameters for performing the method. Thus, the system 100 may receive a specification of target physiologic parameters (e.g., venous SvO2, arterial pCO2, etc.). The system 100 can still further receive fuzzy logic inputs, outputs, and rules, such as for determining outputs in response to measured inputs, as described above. Still further, the system 100 can receive boundaries or limits of various parameters and outputs, such as upper or lower limits of blood flow, gas flow, and blood-to-gas flow ratio. Still further yet, the system 100 can perform steps of the method, such as determining blood flow using fuzzy logic as described above to achieve venous SpO2 targets. Similarly, the system 100 can perform steps of the method for determining gas flow using fuzzy logic as described above to achieve exhaust $CO_2$ targets. Furthermore, the system 100 is configured to store and/or communicate data and parameters (e.g., blood flow targets, gas flow targets, outputs, etc.), such as using internal or external data storage or by remote connection.

With respect to certain aspects of an embodiment, and with continued reference to FIG. 2, the system 100 is configured to automatically control the blood flow and gas flow through a gas exchanger 102 to maintain targeted physiologic parameters in response to sensor inputs. Broadly, system 100 includes a microcontroller 202, sensors (e.g., blood oxygen sensor 110 and blood flowmeter 112), gas flow regulator 140 (including a sweep gas flowmeter 142), an exhaust gas system 150 (including a gas exchanger $CO_2$ sensor 120), and a blood flow regulator 160.

In accordance with certain aspects of an embodiment, the microcontroller 202, as discussed above, may comprise an Arduino Due or other controller, which is configured to perform steps of the method. Furthermore, the microcontroller 202 communicates with other components of the system via a circuit board. For example, the circuit board allows the microcontroller 202 to receive data and inputs (e.g., from the sensors or external system, respectively), as discussed below, and to send instructions to the gas flow regulator 140 and blood flow regulator 160. In certain configurations, the sensors can include sweep gas flowmeter 142, blood flow sensor 112, $CO_2$ sensor 120, and blood oxygen sensor 110 (e.g., an oxyhemoglobin saturation sensor, such as from Medtronic), which are further described below.

In certain configurations, gas flow regulator 140 includes a valve 143, a motor 144 such as a stepper motor coupled to a motor driver, and gas flowmeter 142. Valve 143 may be a needle valve, for example, or other types of valves configured to vary the sweep gas flow rate in response to an input. The input from a sensor (e.g., from gas flowmeter 142, such as a Fathom GR series flowmeter) or sensors (which may be a component of the gas flow regulator 140, or alternatively, a component of an ECMO device, etc.) provides data for the microcontroller 202, as described above. Motor 144 may adjust valve 143 via a motor driver that receives instructions from the microcontroller 202.

In certain configurations, blood flow regulator 160 is configured to operate with an ECMO device, or the like. Thus, blood flow regulator 160 may include a motor driver 162, such as an electronically variable motor controller, a digital-to-analog converter 164 (DAC; e.g., Adafruit MCP4725 Breakout Board—12-Bit DAC w/I2C Interface [ADA935]) in communication with the motor driver 162 and the microcontroller 202, and a blood flowmeter 166 (such as a Transonic flowmeter) receiving a signal from blood flow sensor 112. In other configurations, blood flowmeter 160 may be a component of an ECMO device. Furthermore, motor driver 162 may also be a component of an ECMO device, and it may be configured to accept an offset voltage.

In certain configurations, exhaust gas system 150 is configured to measure the CO2 level (i.e., capnography) of the exhaust gas from gas exchanger 102. For example, the exhaust gas system may include CO2 sensor 120 (such as a SPRINT-IR 20% CO2 meter [GC-0017], which may also be integrated with other components), air pump 152 (e.g., a diaphragm pump) used to sample the exhaust gas, and a dehumidification system including nafion tubing 154 (and more preferably a nafion tubing coil), to couple CO2 sensor 120, the gas exchanger 102 (e.g., an ECMO device), and the controller 200, as necessary. The dehumidification system can further include fan 156 for air circulation, and water trap 158 to remove water from the system. Although the exhaust gas system 150 is described as a separate component, it may be integrated or configured as a component of other devices, such as an ECMO device.

According to certain features of an embodiment, the system and method include system logic. For example, the logic includes determining the blood flow, determining gas flow, and detecting and correcting for undesired conditions. Determining blood flow includes reading the SpO2 of an inlet blood stream entering gas exchanger 102 (e.g., an oxygenator or external ECMO device). If the SpO2 is below a saturation target (e.g., 70% saturated) or a saturation target range, the system may increase the target blood flow through the oxygenator. The target blood flow is increased by the microcontroller 202, which reads the current blood flow and sends instructions to the blood flow regulator 160 to adjust the speed of the blood flow motor 104 (such as according to the method described above) to meet the new blood flow target. However, if the SpO2 is above the target or the saturation target range, the system may decrease the target blood flow accordingly. Further, if the SpO2 is within the target range, no change to blood flow is made. In certain configurations, the microcontroller 202 may use other factors such as determining the rate of change of SpO2, the persistence of an out-of-range SpO2, heart rate, peripheral oxyhemoglobin saturation, as well as other measureable parameters, to define rules (e.g., which the system implements to determine the appropriate response).

Figure 3:
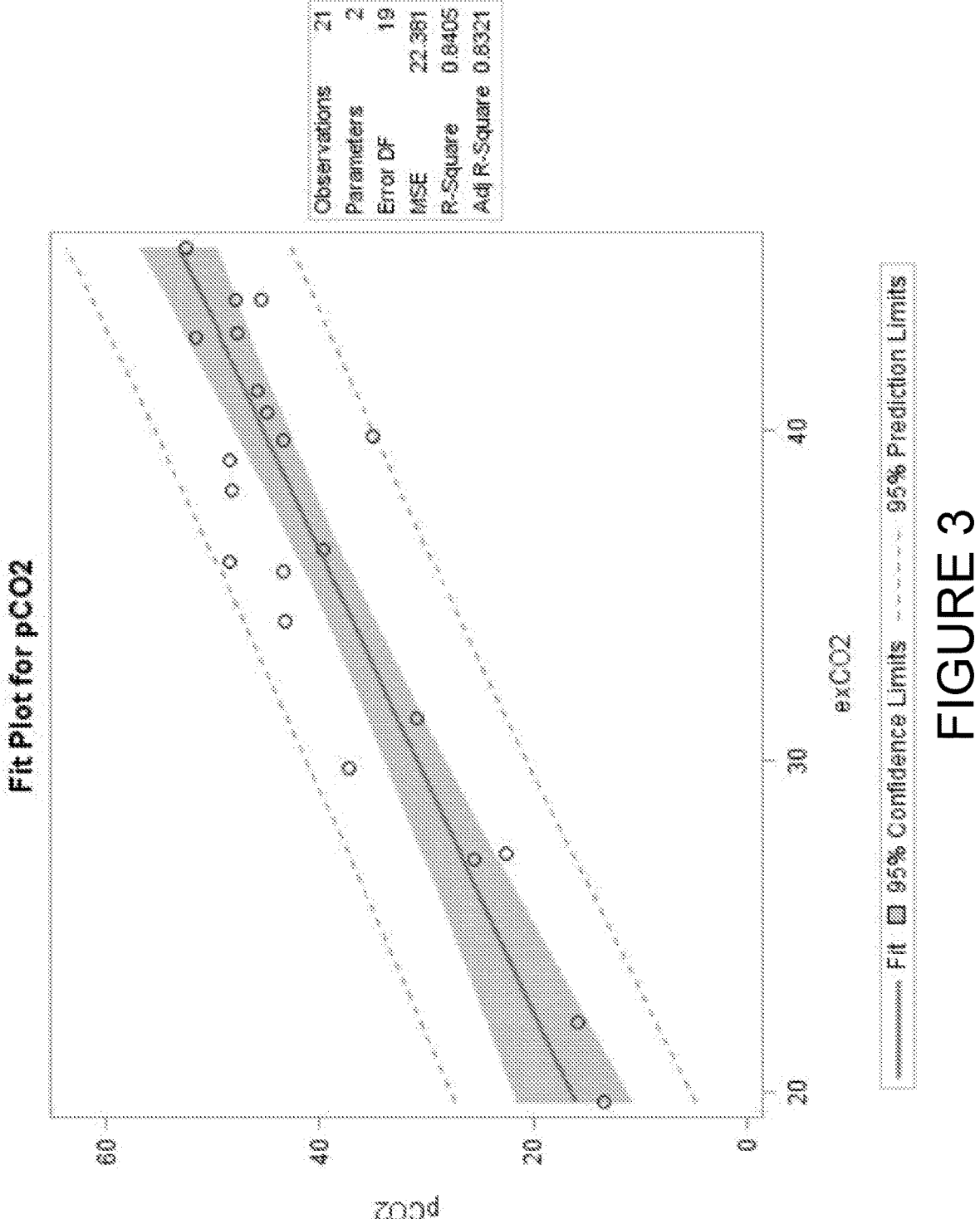
FIG. 3 is a graph of data points produced by operating a system according to certain aspects of an embodiment of the present invention, for regression analysis.

In certain configurations, determining the gas flow may include determining a ratio of blood flow to gas flow. The system 100 may periodically or continuously measure exhaust gas CO2 (i.e. oxygenator exhaust capnography, as described above), and determine an estimated arterial pCO2, such as by using a regression equation described above (see also FIG. 3). If the estimated arterial pCO2 is above the desired target, the system is configured to decrease the blood:gas flow ratio (i.e, the gas flow is increased relative to the blood flow, such as by increasing the flow of exhaust gas or sweep gas). If the estimated arterial pCO2 is below the desired target, the blood:gas flow ratio increases (such as by decreasing the flow of exhaust gas or sweep gas). However, if the estimated arterial pCO2 is within the target range, no change is made to the blood:gas flow ratio.

In certain configurations, system 100 may detect and correct for undesired conditions, including suckdown, insufficient sweep gas, and a safe mode. Suckdown (e.g., venous drainage obstruction) occurs when there is insufficient blood flowing into the pump, either due to obstruction of the inflow cannula or collapse of the venous system or atrium. Thus, suckdown creates a blood flow stream that rapidly reduces flow, then spontaneously resumes blood flow. The system 100 may be configured to detect suckdown by measuring variability in the blood flow by computing a variance of a set of previous measurements. For example, system 100 may compute the variance of the last 10 measurements, although larger or smaller sets can be used, as statistically feasible. If the computed variance is greater than a specific threshold, system 100 sends instructions to reduce the blood flow. However, other techniques to detect suckdown can be used, such as monitoring the pump inlet for pressure changes (e.g., suckdown would cause an increase in negative pressure), and monitoring for acute changes to flow (e.g., suckdown shows a rapid change to ~0LPM for a few seconds prior to resuming).

System 100 may further detect and correct for insufficient sweep gas flow for a target blood flow. For example, if the arterial pCO2 is low, system 100 may automatically reduce the amount of CO2 removed by increasing the blood:gas flow ratio (i.e. reducing the gas flow relative to the blood flow), but below a maximum blood:gas flow ratio (which may be the target blood:gas flow ratio). An undesired situation can arise if the blood:gas flow ratio is increased above a maximum blood:gas flow ratio, which may be necessary to deliver a sufficient amount of oxygen. In certain configurations, system 100 may be further configured to detect insufficient sweep gas flow, such as by examining the oxygenator outlet oxyhemoglobin saturation, and by examining the boundaries of the blood:gas flow ratio and the boundary of the gas flow to determine if the blood:gas flow ratio computed by the arterial pCO2 is lower than a safe threshold.

System 100 may further detect for insufficient blood flow in the setting of adequate oxygenation but elevated pCO2. For example, if the oxygen saturation is above the set-point, the blood flow will attempt to reduce. However, this reduced blood flow may not deliver adequate CO2 to the gas exchanger 102 to allow sufficient CO2 to be removed. In this case, system 100 detects an elevated exhaust gas CO2 concentration in the setting of a low blood flow, and increases the minimum allowable blood flow to ensure enough blood is delivered to the gas exchanger to allow CO2 removal.

System 100 may be further configured to detect and correct for when exhaust gas CO2 concentration cannot be measured, or when system 100 detects error in the exhaust CO2 measurement. In certain configurations, when system 100 cannot measure the exhaust gas CO2 concentration or detects an error in the exhaust CO2 measurement, system 100 may enter a safety mode ("Limp mode"). In the safety or Limp mode, system 100 sets the blood:gas flow ratio to 1:1.

Figure 4:
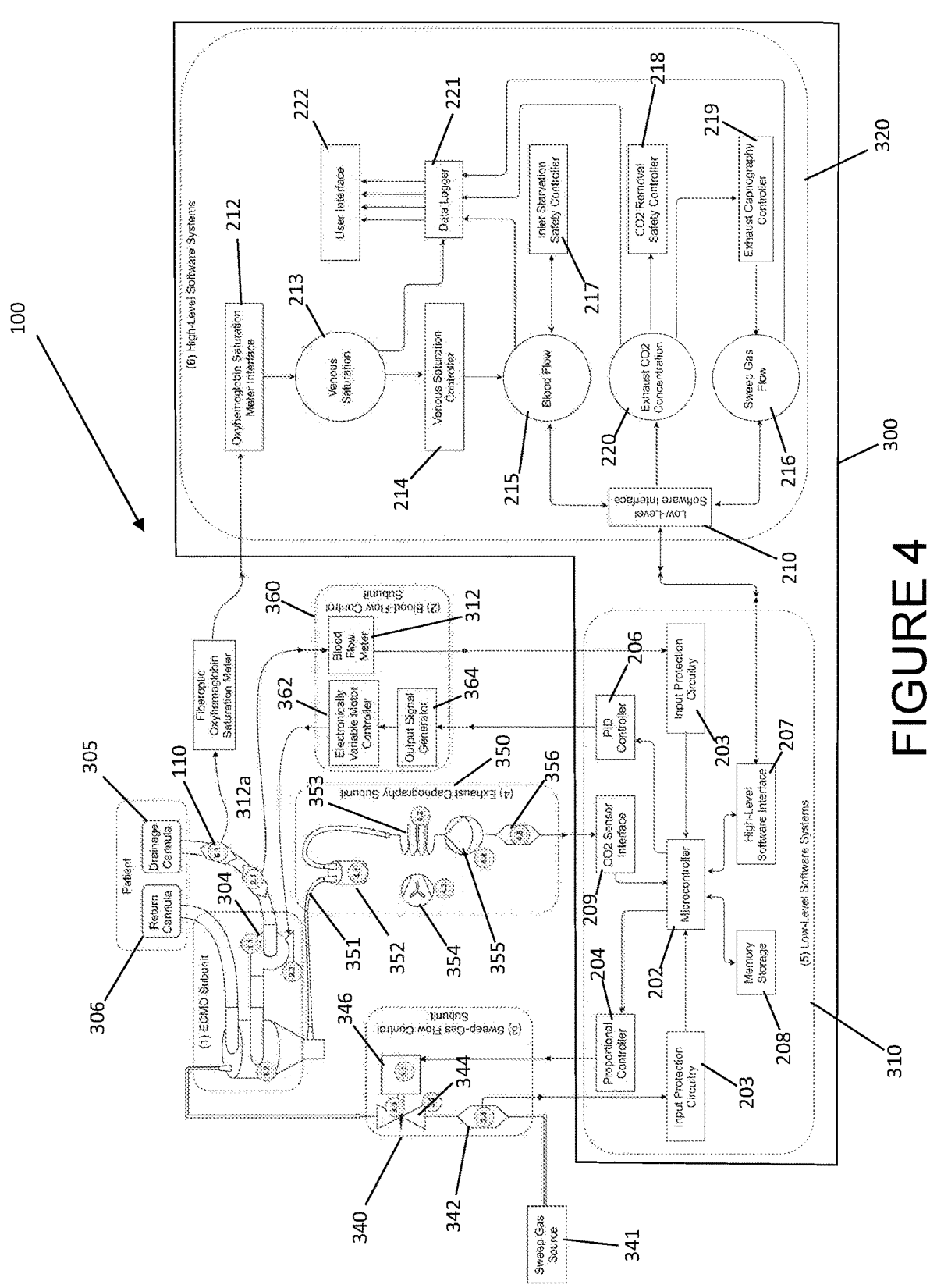
FIG. 4. is a schematic view of an auto-regulatory system for the control of a blood gas exchanger according to further aspects of an embodiment of the invention.

Next, with reference to FIG. 4 and in accordance with certain aspects of a particularly preferred embodiment, adaptive system 100 (e.g., for ECMO) may comprise six major subunits, as described below.

A gas exchanger 302, such as an ECMO unit, may be provided including an artificial pump-lung device that provides the necessary oxygen delivery and CO2 removal activities of system 100. This component drains deoxygenated blood through a drainage cannula 305 positioned in the patient's right atrium (although other cannulation sites can be used, such as femoral vein, as known in the art), which is received by blood pump 304. Blood pump 304 then pushes the blood through the gas exchanger 302, which operating as an oxygenator can include a bundle of hollow polymethylpentene fibers (although other oxygenator materials can be used, as known in the art). Upon exiting the gas exchanger 302, the blood is rich in oxygen and has a normal CO2 concentration, and it is delivered via a return cannula 306 to the patient's pulmonary artery (although other cannulation sites can be used, such as the aorta, internal jugular vein, femoral artery, etc., as known in the art).

A blood flow control unit 360 may be provided including blood flow meter 312, electronically variable motor controller 362, and output signal generator 364. Blood flow control unit 360 is configured to read the blood flow rate via the blood flow meter 312, which is received by a low-level software system 310 of controller 300. Low-level software system 310 determines an appropriate output signal necessary to achieve the desired blood flow rate. The output signal generator 364 (e.g., DAC) may receive a signal from a PID Controller 206, convert the desired signal to the appropriate output voltage, and electronically variable motor controller 362 may adjust the rotating speed of blood pump 304 accordingly.

A sweep gas flow control unit 340 may be provided in fluid communication with a sweep-gas source 341, and includes a gas flow meter 342, a gas flow-control valve 344, a stepper motor 346 with control circuitry, and a coupling between the output of stepper motor 346 and the flow-control valve 344. Sweep gas flow control unit 340 is configured to read the gas flow rate from the gas flow meter 342, which is received by the low level software system 310. The low level software system 310 determines an appropriate valve position for flow-control valve 344 that is required to obtain the desired gas flow rate. The low level software system 310 instructs the circuitry of the stepper motor 346 to adjust the position of the stepper motor 346. The stepper motor 346 rotates position, and through the coupling the flow-control valve 344 is rotated. Thus, the sweep gas flow control unit 340 adjusts the flow delivered by the sweep-gas source 341, thereby adjusting the sweep gas flow rate.

An exhaust capnography unit 350 may be provided including a sampling tube 351, a water trap 352, a length of Nafion tubing 353 for dehumidification, a fan 354, a diaphragm-type air pump 355, and an infrared-based CO2 concentration sensor 356. The diaphragm-type air pump 355 draws a sample of air through the sampling tube 351, water trap 352, and Nafion tubing 353, and delivers it to the infrared-based CO2 concentration sensor 356. The water trap 352 removes large collections of condensation during sampling. The Nafion tubing 353 is coiled in front of fan 354 to provide constant dehumidification of the sample prior to introduction to the infrared-based CO2 concentration sensor 356. The low level software system 310 receives the output from the infrared-based CO2 concentration sensor 356.

The low level software system 310 may include microcontroller 202, input protection circuitry 203 for the blood flowmeter 312 and gas flowmeter 342, software-implemented PID controller 206 for blood flow control, software-implemented proportional controller 204 for gas flow control, an interface 207 for communication with high level software systems 320, and long-term memory storage 208. Low level software system 310 preferably measures and controls (closed-loop) blood flow and sweep gas flow, as well as measuring exhaust gas CO2 concentration through CO2 sensor interface 209. Low level software system 310 may send measurements to high level software system 320 for further processing, as discussed below. Low level software system 310 can further receive commands or instructions from high level software system 320 to determine the blood flow and sweep gas flow set points.

High level software system 320 may include an interface 210 for bi-directional communication with low-level software system 310, along with a number of logical elements that receive data from sensors in system 100, maintain physiologic set points and target output parameters, and process the received data to optimize such output parameters. More particularly, high level software system 320 includes an interface 212 for communication with an oxyhemoglobin saturation monitor, which communicates a patient's venous oxygen concentration 213 to a venous oxygen concentration controller 214, which in turn is in data communication with a Fuzzy Model Reference Learning Controller (FMRLC) 215 for self-improving control of blood flow. Further, high level software system 320 includes a FMRLC 216 for self-improving control of sweep-gas flow. A safety limit controller 217 is provided to prevent pump inlet starvation (suckdown), and a safety limit controller 218 is provided to prevent insufficient CO2 removal in high saturation states. Sweep gas flow FMRLC 216 may likewise receive control signals from an exhaust capnography controller 219, which in turn receives exhaust CO2 concentration data 220. A data logger 221 may be provided to log all data that is recorded or computed by system 100, and a user interface 222 may be provided to display measurement readings, physiologic set points, and target output parameters.

Each of low level software system 310 and high level software system 320 may be implemented on a personal computer or similarly configured computing device, each of which may be configured to automatically save configurations.

The closed-loop processing system is configured to receive measurements of oxygenator inlet oxyhemoglobin saturation and oxygenator exhaust CO2 concentration. Using these inputs, the system calculates error in oxyhemoglobin saturation and CO2 concentration, and a first derivative of these errors with respect to time. These parameters may then be assessed by the corresponding FMRLCs to determine changes to blood flow that are necessary to reduce the oxygenator inlet oxyhemoglobin saturation error, or the change to sweep gas necessary to reduce the oxygenator exhaust gas CO2 concentration error.

As mentioned above, high level software system 320 may use a fuzzy controller for both the blood flow and sweep gas flow systems to decide on the appropriate output adjustments. The low level software system 310 receives the output adjustments via the communication interface, and the low level software system 310 adjusts the blood flow and sweep gas flow accordingly, as discussed above. The fuzzy controllers are considered Fuzzy Model Reference Learning Controllers (FMRLCs) because each adjustment is compared to the mathematical model of an "ideal" response (based on the transient response of a second-order system to a step input) and the FMRLC adjusts the response characteristics to attempt to achieve a response that is closer to the "ideal" response. User interface 222 displays relevant parameters to the end user, and the program logs data accordingly. Safety mechanisms 217 and 218 are in place to prevent pump inlet starvation (e.g., by measuring the blood flow variance and actual blood flow versus requested or targeted blood flow), and to prevent inadequate $CO_2$ removal in situations where there is adequate oxyhemoglobin saturation.

Experimental Embodiments

Validation and verification of a system and method according to certain aspects of an embodiment of the invention included experimental studies and analysis. These studies may lead to the development of an ECMO system that senses the gas-exchange requirements of the patient, and adapts the level of support accordingly. A system and method in accordance with certain aspects of an embodiment for a demand-adapting ECMO will provide superior support to conventional ECMO, such as in the setting of long-term therapy in ambulating patients. When applied to a portable ECMO system, such demand-adapting logic will increase patient mobility.

Figure 5:
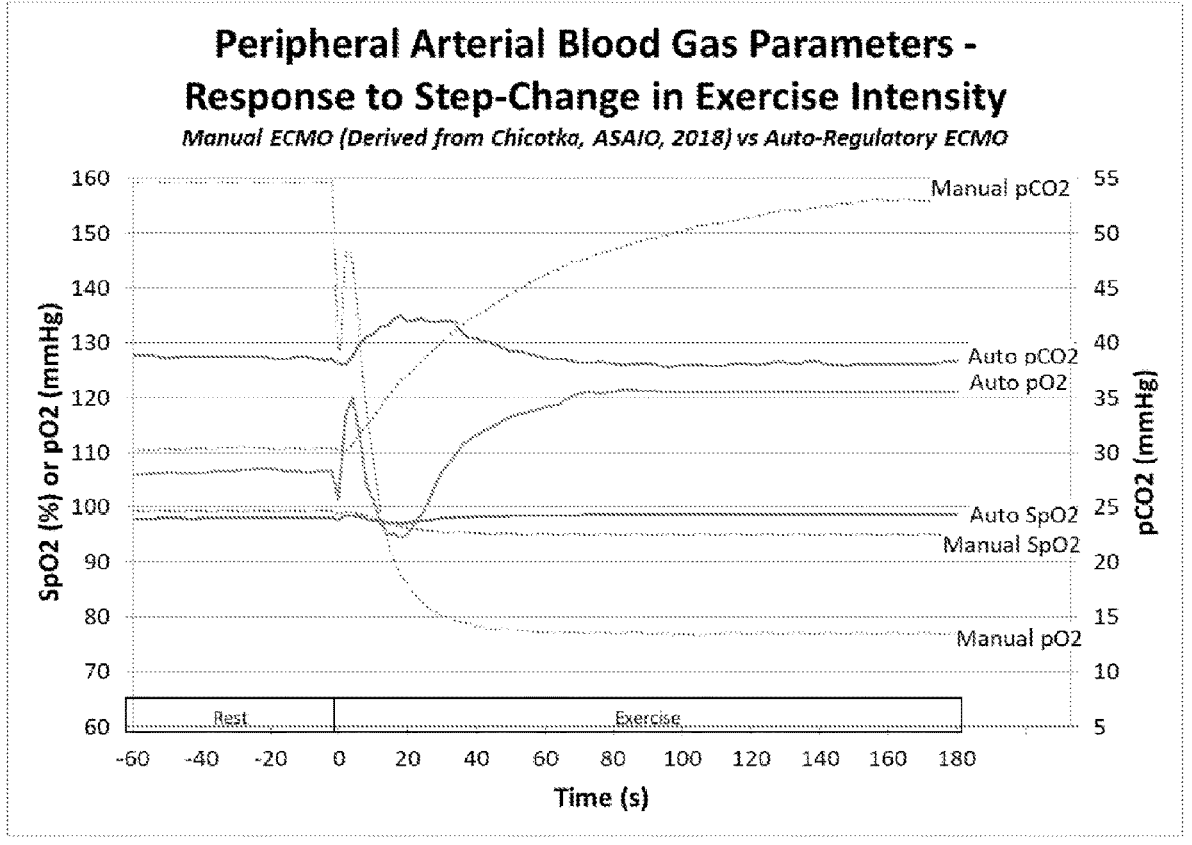
FIG. 5 is a graph showing results of one embodiment of the systems of FIGS. 2 and 4 compared to typical ECMO systems.
Figure 6:
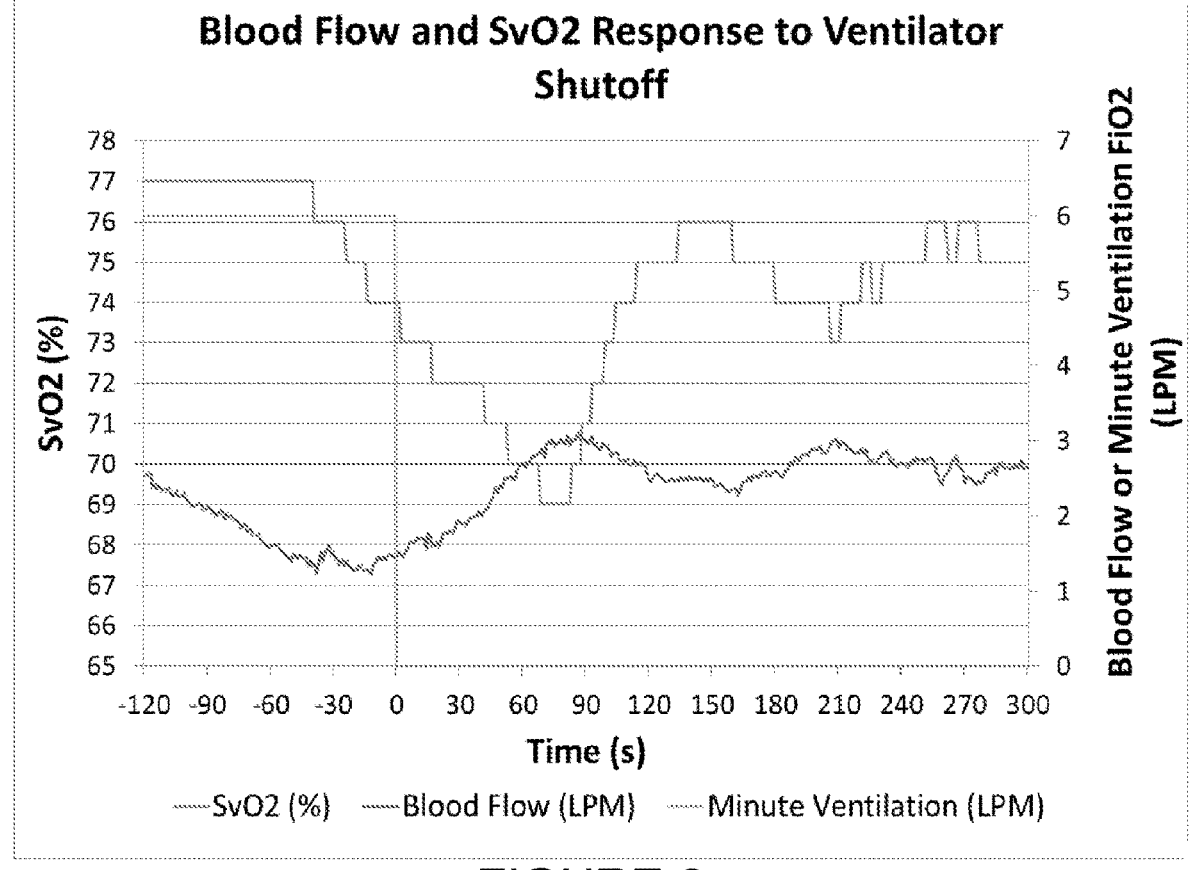
FIG. 6 is a graph showing experimental results of SvO2 and blood flow rate in response to a ventilator shutoff while using an embodiment of the system and method.
Figure 7:
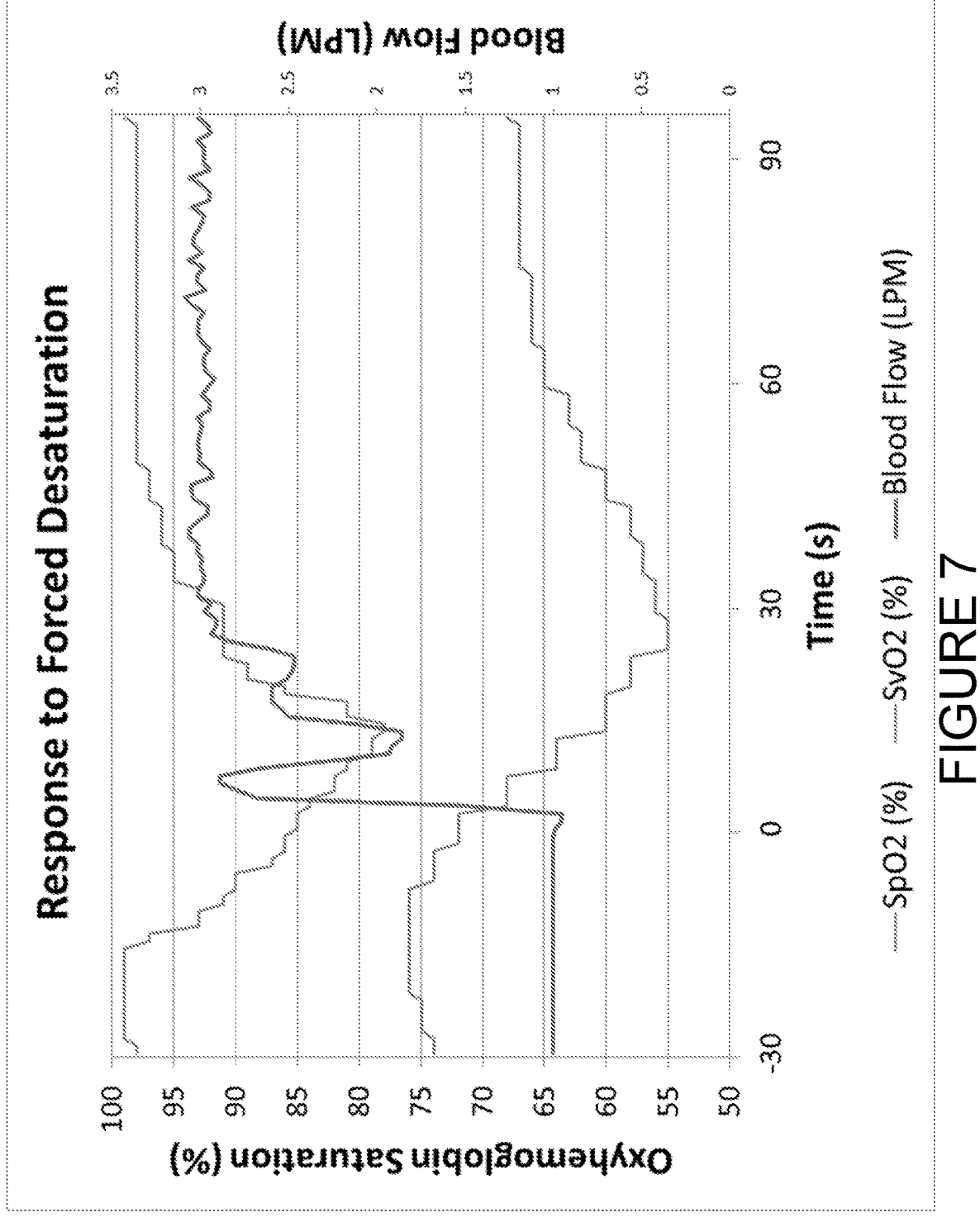
FIG. 7 is a graph showing experimental results of a response of SvO2, SpO2, and blood flow to forced desaturation while using an embodiment of the system and method.

In verification and validation, ovine models previously cannulated with an artificial lung device were attached to an embodiment of the system and evaluated, as discussed below, for at least 90 minutes without deleterious effect on the animal. In another evaluation, and with reference to FIG. 5, a simulated experiment was conducted to generate simulated results including four ovine experiments of 6 hours duration on auto-regulatory ECMO to assess response to exercise while on conventional ECMO versus adaptive ECMO. Those experiments included ventilator shutoff, forced desaturation, and ventilator off-on-off disturbances. Furthermore, FIGS. 6 and 7 show responses of SvO2 and blood flow rate, and a response of SvO2, SpO2, and blood flow to forced desaturation (respectively) while using one embodiment of the system and method.

An experiment was conducted to verify a system configured to adapt to gas exchange demands in an ovine model. This experiment demonstrates the ability of a system (an ECMO circuit) to adapt to variation in metabolic demands. The control system and ECMO circuit are used as a basis for both partial and complete cardiopulmonary support in animals with compromised cardiopulmonary function in an acute study lasting 6 hours.

The purpose of this study was to evaluate the adaptive, auto-regulatory artificial lung in an ovine model over a 6 hour period. Endotracheal FiO2 and minute ventilation are modified to test system adaptive ability.

The study was carried out as follows:

1. Perform surgical cannulation from RA to PA and connect to pre-built device.

2. Verify device functionality and measure upper blood flow limit.

3. Set software to Manual Mode, with blood flow at 80% of upper blood flow limit, and gas flow: blood flow ratio at 1:1.

4. Turn on data logging in software.

5. Transition from Isofluorane anesthesia to propofol anesthesia, with a Propofol CRI 180-400 mcg/kg/min.

6. Set endotracheal gas blender to FiO2 of 100%, and match tidal volume and respiratory rate to anesthesia machine. (Acceptable tidal volume is 8-15 mL/kg, acceptable respiratory rate is ~12 respirations/min).

7. Discontinue endotracheal tube from anesthesia machine, and connect to blended ventilator.

8. Set software to Adaptive Mode, with goal venous SpO2 of 70% and goal exhaust CO2 of 40 mmHg.

9. Reduce respiratory rate by 2 respirations/min every 1 minute until 1 respiration/min is achieved. Record vital signs, device parameters and ventilator parameters at the end of each adjustment. Return to 12 respirations/min if there are any deleterious findings in the vital signs.

10. Reduce the FiO2 in the gas blender by increments of 10% every 1 minute until the FiO2 reaches 0%. Keep the CO2 concentration at 0% at this time, so the endotracheal gas should be 100% N2. Record vital signs, device parameters and ventilator parameters at the end of each adjustment. Return to 12 respirations/min and 100% FiO2 if there are any deleterious findings in the vital signs.

11. Continue autoregulatory total artificial lung support-set experiment end-time for 6 hours from now.

12. Measure the following continuously: Heart Rate, Blood Pressure, Mean Arterial Pressure, Peripheral SpO2, etCO2, Blood Flow, Gas Flow, Oxygenator Inlet SpO2, Oxygenator Outlet SpO2, Exhaust Gas CO2, Ventilator FIO2, Tidal Volume, Respiratory Rate.

13. For the first 1 hour, measure the following Every 15 minutes: Peripheral Arterial Blood Gas, Oxygenator Inlet Blood Gas, Oxygenator Outlet Blood Gas, Electrolytes (if available), and Lactate (if available).

14. For Hours 2 through 6, measure the following Every 30 minutes: Peripheral Arterial Blood Gas, Oxygenator Inlet Blood Gas, Oxygenator Outlet Blood Gas, Electrolytes (if available), and Lactate (if available).

15. Measure Activated Clotting Time (ACT) every 1 hour and adjust heparin infusion to maintain ACT between 190-210 seconds.

16. If relative stability is observed during hours 2 through 6, provide step disturbances to the system (turn ventilator on and then off again; force a desaturation and allow the system to recover).

The foregoing study confirmed that systems and methods in accordance with at least certain aspects of an embodiment of the invention may provide ambulatory artificial lung support to a patient without the use of invasive sensors placed in the patient's body through an automatically adapting ECMO system. Such a system may manage patient oxygenation and blood carbon dioxide levels, maintaining physiologic targets using measurements from the artificial lung device as inputs, and in turn reducing the need for invasive sensors.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. An auto-regulatory system for the control of a blood gas exchanger comprising:

a blood gas exchanger having a blood inlet, a blood outlet, a gas inlet, and a gas outlet;

an oxygen sensor positioned to detect oxyhemoglobin saturation at said blood inlet;

a carbon dioxide sensor positioned to detect exhaust gas CO2 concentration at said gas outlet;

a fluid pump in fluid communication with said blood gas exchanger;

a gas delivery system in fluid communication with said blood gas exchanger; and a controller comprising a microcontroller and memory storage having computer-executable instructions stored thereon, wherein when executed by the microcontroller, the computer-executable instructions cause the controller to:

receive real-time data from the oxygen sensor and the carbon dioxide sensor;

process the received real-time data by using a fuzzy logic control algorithm (FLCA) that (i) reads oxygenator inlet oxyhemoglobin saturation and oxygenator exhaust gas CO2 concentration to determine errors from set-point values and a first derivative of the errors with respect to time, (ii) converts the errors and first derivatives into fuzzy inputs through fuzzification, and (iii) applies membership function evaluation and defuzzification to determine adjustments for maintaining the sensed oxygen and carbon dioxide levels within target ranges to determine optimal adjustment parameters for maintaining physiologic parameters within target ranges; and dynamically adjust the fluid pump speed and the gas flow rate based on the processed real-time data to maintain the sensed oxygen and carbon dioxide levels within pre-designated target ranges that are adjustable based on a patient's instantaneous metabolic demands.

2. The system of claim 1, wherein said computer-executable instructions are further configured to analyze the real-time data to determine an optimal blood:gas ratio and adjust at least one of carbon dioxide flow and blood flow to maintain the optimal blood:gas ratio within the determined optimal target range.

3. The system of claim 1, said gas delivery system further comprising a valve, a motor operatively engaging the valve, and a gas flowmeter.

4. The system of claim 3, wherein said computer-executable instructions are configured to analyze said sensed oxygen level and said sensed carbon dioxide level to determine optimal valve positioning parameters and adjust operation of said motor to modify a position of said valve based on the determined optimal valve positioning parameters.

5. The system of claim 1, further comprising a blood flow regulator having a motor driver in electrical communication with said fluid pump, and a blood flow sensor positioned to measure blood flow within a drainage cannula from a patient.

6. The system of claim 5, wherein said computer-executable instructions are configured to analyze at least one of said sensed oxygen level, said sensed carbon dioxide level, and a sensed blood flow level by said blood flow sensor to determine optimal pump operation parameters and adjust operation of said fluid pump through said motor driver based on the determined optimal pump operation parameters.

7. The system of claim 1, further comprising an exhaust gas system comprising said carbon dioxide sensor, an air pump, and a dehumidification system.

8. The system of claim 7, wherein said computer-executable instructions are configured to analyze said sensed carbon dioxide level to determine optimal exhaust system operation parameters and adjust operation of at least one of said gas delivery system and said fluid pump based on the determined optimal exhaust system operation parameters.

9. An auto-regulatory system for the control of a blood gas exchanger comprising:

a blood gas exchanger having a blood inlet, a blood outlet, a gas inlet, and a gas outlet;

an oxygen sensor positioned to detect oxyhemoglobin saturation at said blood inlet;

a carbon dioxide sensor positioned to detect exhaust gas CO2 concentration at said gas outlet; and a controller comprising a microcontroller and memory storage having computer-executable instructions stored thereon, wherein when executed by the microcontroller, the computer-executable instructions cause the controller to:

receive real-time data from the oxygen sensor and the carbon dioxide sensor;

process the received real-time data by analyzing the real time data to determine using a fuzzy logic control algorithm (FLCA) that (i) reads oxygenator inlet oxyhemoglobin saturation and oxygenator exhaust gas CO2 concentration to determine errors from set-point values and a first derivative of the errors with respect to time, (ii) converts the errors and first derivatives into fuzzy inputs through fuzzification, and (iii) applies membership function evaluation and defuzzification to determine adjustments for maintaining the sensed oxygen and carbon dioxide levels within target ranges to determine optimal adjustment parameters for maintaining physiologic parameters within target ranges; and dynamically adjust blood flow and gas flow through the blood gas exchanger based on the processed real-time data to maintain said sensed oxygen and carbon dioxide levels within pre-designated target ranges that are adjustable based on a patient's instantaneous metabolic demands.

10. The system of claim 9, wherein said computer executable instructions are further configured to analyze the real-time data to determine an optimal blood:gas ratio and adjust at least one of carbon dioxide flow and blood flow to maintain the optimal blood:gas ratio within the determined optimal target range.

11. The system of claim 9, further comprising a gas delivery system having a valve, a motor operatively engaging the valve, and a gas flowmeter.

12. The system of claim 11, wherein said computer executable instructions are configured to analyze said sensed oxygen level and said sensed carbon dioxide level to determine optimal valve positioning parameters and adjust operation of said motor to modify a position of said valve based on the determined optimal valve positioning parameters.

13. The system of claim 9, further comprising:

a fluid pump; and a blood flow regulator having a motor driver in electrical communication with said fluid pump, and a blood flow sensor positioned to measure blood flow within a drainage cannula from a patient.

14. The system of claim 13, wherein said computer-executable instructions are configured to analyze at least one of said sensed oxygen level, said sensed carbon dioxide level, and a sensed blood flow level by said blood flow sensor to determine optimal pump operation parameters and adjust operation of said fluid pump through said motor driver based on the determined optimal pump operation parameters.

15. The system of claim 9, further comprising an exhaust gas system comprising said carbon dioxide sensor, an air pump, and a dehumidification system.

16. The system of claim 15, wherein said computer-executable instructions are configured to analyze said sensed carbon dioxide level to determine optimal exhaust system operation parameters and adjust operation of at least one of gas delivery to said blood gas exchanger and blood delivery to said blood gas exchanger based on the determined optimal exhaust system operation paramters.

17. A method for autoregulation of a blood gas exchanger, comprising the steps of:

providing a blood gas exchanger having a blood inlet, a blood outlet, a gas inlet, and a gas outlet; an oxygen sensor positioned to detect oxyhemoglobin saturation at said blood inlet; a carbon dioxide sensor positioned to detect exhaust gas CO2 concentration at said gas outlet; and a controller comprising a microcontroller and memory storage having computer-executable instructions stored thereon, wherein when executed by the microcontroller, the computer-executable instructions cause the controller to:

receive real-time data from the oxygen sensor and the carbon dioxide sensor;

process the received real-time data by using a fuzzy logic control algorithm (FLCA) that (i) reads oxygenator inlet oxyhemoglobin saturation and oxygenator exhaust gas CO2 concentration to determine errors from set-point values and a first derivative of the errors with respect to time, (ii) converts the errors and first derivatives into fuzzy inputs through fuzzification, and (iii) applies membership function evaluation and defuzzification to determine adjustments for maintaining the sensed oxygen and carbon dioxide levels within target ranges to determine optimal adjustment parameters for maintaining physiologic parameters within target rangers; and dynamically adjust blood flow and gas flow through the blood gas exchanger based on the processed real-time data to maintain said sensed oxygen and carbon dioxide levels within pre-designated target ranges that are adjustable based on a patient's instantaneous metabolic demands;

receiving at said controller a blood flow rate of blood flowing to said blood gas exchanger and a sweep gas flow rate of sweep gas flowing to said blood gas exchanger;

receiving at said controller a blood oxygen concentration from said oxygen sensor;

receiving at said controller an exhaust gas CO2 concentration from said carbon dioxide sensor; and causing said controller to modify at least one of said blood flow rate and said sweep gas flow rate in response to and based upon said blood oxygen concentration and said exhaust gas CO2 concentration.

18. The method of claim 17, further comprising the step of determining at said controller an estimated blood CO2 concentration based upon said exhaust gas CO2 concentration.

19. The method of claim 18, further comprising the step of causing said controller to modify a blood:gas flow ratio in response to and based upon said determining an estimated blood CO2 concentration.

* * * * *